United States Patent
Lee et al.

(10) Patent No.: US 11,408,018 B2
(45) Date of Patent: Aug. 9, 2022

(54) FRUCTOSE-C4-EPIMERASE AND PREPARATION METHOD FOR PRODUCING TAGATOSE USING THE SAME

(71) Applicant: CJ CheilJedang Corporation, Seoul (KR)

(72) Inventors: Young Mi Lee, Seoul (KR); Il Hyang Park, Seoul (KR); Sun Mi Shin, Seoul (KR); Sungjae Yang, Seoul (KR); Hyun Kug Cho, Seoul (KR); Seong Bo Kim, Seoul (KR); Eun Jung Choi, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/640,341

(22) PCT Filed: Aug. 31, 2018

(86) PCT No.: PCT/KR2018/010123
§ 371 (c)(1),
(2) Date: Feb. 19, 2020

(87) PCT Pub. No.: WO2019/045510
PCT Pub. Date: Mar. 7, 2019

(65) Prior Publication Data
US 2020/0263217 A1 Aug. 20, 2020

(30) Foreign Application Priority Data
Aug. 31, 2017 (KR) .................. 10-2017-0111489

(51) Int. Cl.
*C12P 19/02* (2006.01)
*C12N 9/90* (2006.01)

(52) U.S. Cl.
CPC ......... *C12P 19/02* (2013.01); *C12Y 401/0204* (2013.01)

(58) Field of Classification Search
None
See application file for complete search history.

(56) References Cited

U.S. PATENT DOCUMENTS

2016/0186162 A1*  6/2016  Oh .................. C12P 19/02
                                                        435/148
2020/0165639 A1*  5/2020  Zanghellini ......... C12N 15/113

FOREIGN PATENT DOCUMENTS

| EP | 3211078 A1 | 8/2017 |
|---|---|---|
| KR | 10-0964091 B | 6/2010 |
| KR | 10-1368731 B | 2/2014 |
| KR | 10-2014-0143109 A | 12/2014 |
| KR | 10-1480422 B1 | 1/2015 |
| WO | WO 2006/058092 A2 | 6/2006 |
| WO | WO 2017/059278 A1 | 4/2017 |
| WO | WO 2020/010260 A1 | 1/2020 |

OTHER PUBLICATIONS

GenPept Database Accession No. WP_014433578, Jun. 2015, 1 page (Year: 2015).*
Samuel et al., Nat. Prod. Rep. 19:261-277, 2002 (Year: 2002).*
Zhang et al., BioMetals 19:31-37, 2006 (Year: 2006).*
International Search Report and Written Opinion of the International Patent Application No. PCT/KR2018/010123, dated Dec. 10, 2018 together with the English translation of the International Search Report; 16 pages.
Brinkkötter et al., "Two class IID-tagatose-bisphosphate aldolases from enteric bacteria", Archives of Microbiology, 2002, vol. 177, pp. 410-419; DOI 10.1007/S00203-002-0406-6.
Lee et al., "Structure-based prediction and identification of 4-epimerization activity of phosphate sugars in class II aldolases", Scientific Reports, May 16, 2017, vol. 7, article No. 1934, pp. 1-9; DOI:10.1038/S41598-017-02211-3.
DATABASE UniProt [Online] Jun. 13, 2012, "SubName: Full= Putative tagatose 6-phosphate aldolase subunit Z {ECO:0000313 EMBL:BAM00345.1};", XP055755583, retrieved from EBI accession No. UNIPROT:IOI507 Database accession No. I0I507.

* cited by examiner

*Primary Examiner* — David Steadman
(74) *Attorney, Agent, or Firm* — Squire Patton Boggs (US) LLP

(57) ABSTRACT

The present disclosure relates to a composition for producing tagatose comprising a protein having fructose-4-epimerase activity and a method for producing tagatose using the same.

3 Claims, 2 Drawing Sheets
Specification includes a Sequence Listing.

FRUCTOSE-C4-EPIMERASE AND PREPARATION METHOD FOR PRODUCING TAGATOSE USING THE SAME

The instant application is the National Stage of International Application No. PCT/KR2018/010123, filed Aug. 31, 2018, which claims the benefit of Korean application no. 10-2017-0111489, filed Aug. 31, 2017, the contents of which are hereby incorporated by reference in their entireties.

The instant application contains a Sequence Listing which has been filed electronically in ASCII format and is hereby incorporated by reference in its entirety. The ASCII copy, created on Feb. 13, 2020, is named OPA18280 seq_list.txt and is 5,408 bytes in size.

TECHNICAL FIELD

The present disclosure relates to a composition for producing tagatose including a protein having fructose-4-epimerase activity and a method for producing tagatose using the same.

BACKGROUND ART

Tagatose is a natural sweetener, which is present in a small amount in foods such as milk, cheese, cacao, etc., and in sweet fruits such as apples and mandarin. Tagatose has a calorie value of 1.5 kcal/g, which is one third that of sucrose, and a glycemic index (GI) of 3, which is 5% that of sucrose. Tagatose has a physical property and a sweet taste similar to sucrose, and various health benefits. Thus, tagatose can be used in a wide variety of products as an alternative sweetener capable of satisfying both taste and health.

Conventionally known or commonly used methods of producing tagatose include a chemical method (a catalytic reaction) or a biological method (an isomerizing enzyme reaction) using galactose as a main raw material (see PCT WO2006/058092, Korean Patent Nos. 10-0964091 and 10-1368731). However, the price of lactose which is a basic raw material of galactose used as a main raw material in the known production methods was unstable depending on produced amounts, supply, and demand of raw milk and lactose in global markets, etc. Thus, there is a limitation in the stable supply thereof. Therefore, a new method capable of producing tagatose from a commonly used sugar (sucrose, glucose, fructose, etc.) as a raw material has been needed.

DISCLOSURE

Technical Problem

The present inventors have conducted extensive studies to develop an enzyme having activity to convert fructose into tagatose, and as a result, they found that tagatose-bisphosphate aldolase derived from *Caldilinea* sp. has the ability to convert fructose into tagatose, thereby completing the present disclosure.

Technical Solution

An object of the present disclosure is to provide a composition for producing tagatose, including at least one of tagatose-bisphosphate aldolase derived from *Caldilinea* sp., a microorganism expressing the tagatose-bisphosphatealdolase, or a culture of the microorganism.

Another object of the present disclosure is to provide a method of producing tagatose, including converting fructose into tagatose by contacting fructose with at least one of tagatose-bisphosphate aldolase derived from *Caldilinea* sp., a microorganism expressing the tagatose-bisphosphate aldolase, or a culture of the microorganism.

Advantageous Effects

The tagatose-bisphosphate aldolase, which is a fructose-4-epimerase of the present disclosure, has excellent heat-resistance, can produce tagatose in an industrial scale and convert fructose as a common sugar into tagatose, and thus is economically feasible.

DETAILED DESCRIPTION OF PREFERRED EMBODIMENTS

Figure 1:
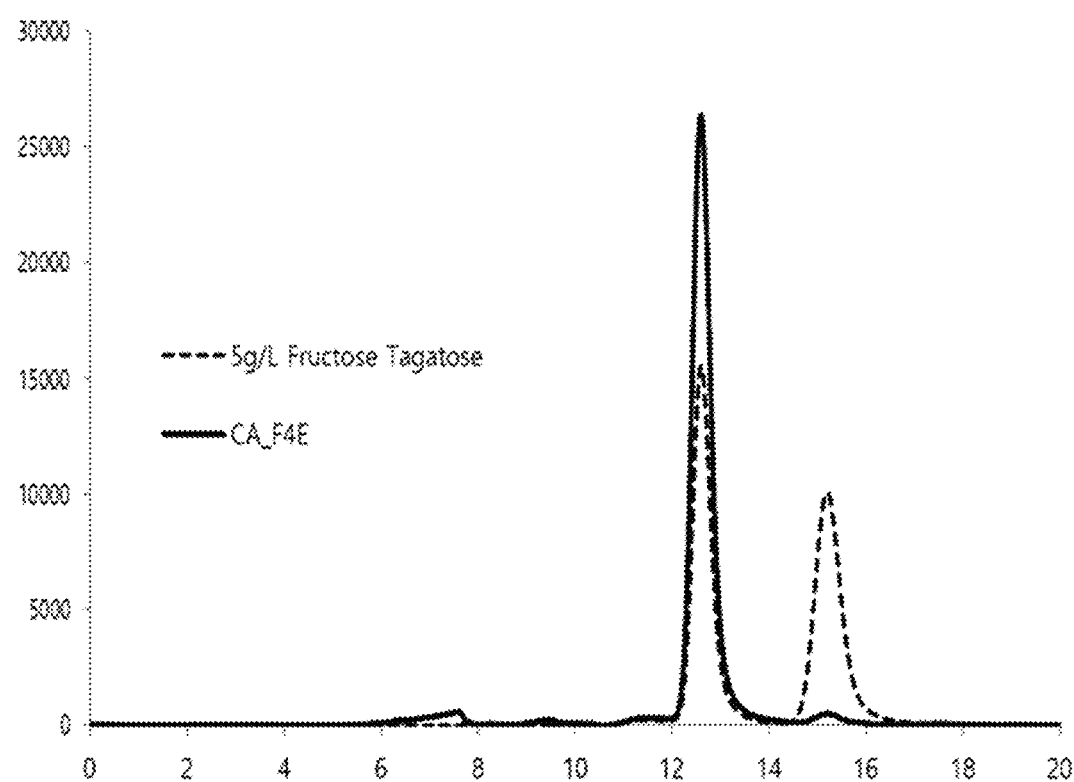
FIG. 1 is a graph of HPLC chromatography showing that tagatose-bisphosphate aldolase (CJ_CA_F4E) of the present disclosure has fructose-4-epimerase activity.

Hereinafter, the present disclosure will be described in detail. Meanwhile, each description and embodiment disclosed herein may be applied to other descriptions and embodiments. That is, all combinations of various elements disclosed in this disclosure fall within the scope of the present disclosure. Additionally, the scope of the present disclosure is not limited by the specific description described below.

Additionally, those of ordinary skill in the art may be able to recognize or confirm, using only conventional experimentation, many equivalents to the particular aspects of the invention described herein. Furthermore, it is also intended that these equivalents be included in the present disclosure.

The present disclosure has newly discovered that tagatose-bisphosphate aldolase has fructose-4-epimerase activity.

The fructose-4-epimerase or a variant thereof is characterized by converting D-fructose into D-tagatose by epimerizing D-fructose at C4 position. It is known that the fructose-4-epimerase has tagatose-bisphosphate aldolase activity, produces glycerone phosphate and D-glyceraldehyde 3-phosphate from D-tagatose 1,6-bisphosphate as a substrate.

Meanwhile, tagatose-bisphosphate aldolase (EC 4.1.2.40) is known to produce glycerone phosphate and D-glyceraldehyde 3-phosphate from D-tagatose 1,6-bisphosphate as a substrate, as shown in the following [Reaction Scheme 1], and to participate in a galactose metabolism. However, there have been no studies regarding whether the tagatose-bisphosphate aldolase has activity to produce tagatose.

[Reaction Scheme 1]
D-tagatose 1,6-bisphosphate<=> glycerone phosphate+ D-glyceraldehyde 3-phosphate The present disclosure newly revealed that the tagatose-bisphosphate aldolase has fructose-4-epimerase activity. Accordingly, one embodiment of the present disclosure provides novel use of tagatose-bisphosphate aldolase including the use of the tagatose-bisphosphate aldolase as a fructose-4-epimerase in the production of tagatose from fructose. Additionally, another embodiment of the present disclosure provides a method for producing tagatose from fructose using the tagatose-bisphosphate aldolase as a fructose-4-epimerase.

In order to achieve the objects of the present disclosure, an aspect of the present disclosure provides a composition for producing tagatose, including at least one of tagatose-bisphosphate aldolase derived from *Caldilinea* sp., a microorganism expressing the tagatose-bisphosphate aldolase, or a culture of the microorganism.

The composition may further include fructose, and the fructose may specifically be D-fructose, but is not limited thereto.

The tagatose-bisphosphate aldolase of the present disclosure may be an enzyme derived from a heat-resistant microorganism or a variant thereof, for example, it may be an enzyme derived from *Caldilinea* sp. or a variant thereof. Specifically, it may be an enzyme derived from *Caldilinea aerophila* DSM 14535 or a variant thereof.

In one embodiment, the tagatose-bisphosphate aldolase of the present disclosure may be an enzyme having high heat resistance. Specifically, the tagatose-bisphosphate aldolase of the present disclosure may exhibit 50% to 100%, 60% to 100%, 70% to 100%, or 75% to 100% of its maximum activity at 50° C. to 70° C. More specifically, the tagatose-bisphosphate aldolase of the present disclosure may exhibit 80% to 100% or 85% to 100% of its maximum activity at 55° C. to 60° C. or 60° C. to 70° C.

In the present disclosure, the tagatose-bisphosphate aldolase may have an amino acid sequence of SEQ ID NO: 1 or an amino acid sequence having an identity of 85% or more thereto.

Specifically, the tagatose-bisphosphate aldolase may have an amino acid sequence of SEQ ID NO: 1 or an amino acid sequence having an identity of 85% or more thereto. For example, any tagatose-bisphosphate aldolase may be used without limitation as long as it is able to produce tagatose from fructose as a substrate. Specifically, the tagatose-bisphosphate aldolase may have a conversion rate (conversion rate=weight of tagatose/initial weight of fructose*100) of 0.01% or more, specifically, 0.1% or more, and more specifically, 0.3% or more from fructose as a substrate into tagatose. More specifically, the conversion rate may be in the range from 0.01% to 40%, from 0.1% to 30%, from 0.3% to 25%, or from 0.3% to 20%.

The tagatose-bisphosphate aldolase of the present disclosure or a variant thereof may be obtained by transforming a strain such as *E. coli* with DNA expressing the enzyme of the present disclosure or a variant thereof, e.g., SEQ ID NO: 2, culturing the strain to obtain a culture, disrupting the culture, and then performing purification using a column, etc. The strain for transformation may include *Corynebacterium glutamicum*, *Aspergillus oryzae*, or *Bacillus subtilis*, etc., in addition to *Escherichia coli*.

According to one embodiment of the present disclosure, the tagatose-bisphosphate aldolase of the present disclosure may include an amino acid sequence having a homology or identity of 85% or more to the amino acid sequence of SEQ ID NO: 1, but is not limited thereto. According to another embodiment, the tagatose-bisphosphate aldolase of the present disclosure may include a polypeptide having a homology or identity of at least 85%, 90%, 95%, 96%, 97%, 98%, or 99% to the amino acid sequence of SEQ ID NO: 1. Additionally, it is apparent that functional fragments having an amino acid sequence with deletion, modification, substitution, or addition in part of the sequence also fall within the scope of the present disclosure as long as the amino acid has such homology or identity and exhibits an efficacy corresponding to the protein.

Additionally, it is apparent that a polynucleotide which can be translated by due to codon degeneracy into a protein consisting of the amino acid sequence of SEQ ID NO: 1 or a protein having a homology or identity thereto can also be included. Alternatively, a probe which can be prepared from a known gene sequence, for example, any sequence which hybridizes with a sequence complementary to all or a part of the nucleotide sequence under stringent conditions to encode a protein having the activity of the protein consisting of the amino acid sequence of SEQ ID NO: 1, may be included without limitation.

The "stringent conditions" refer to the conditions which allow the specific hybridization between the polynucleotides. Such conditions are specifically disclosed in the literature (e.g., J. Sambrook et al., *Molecular Cloning, A Laboratory Manual,* 2nd Edition, Cold Spring Harbor Laboratory press, Cold Spring Harbor, N.Y., 1989; F. M. Ausubel et al., *Current Protocols in Molecular Biology*, John Wiley & Sons, Inc., New York). For example, the stringent conditions may include conditions under which genes having a high homology or identity, a homology or identity of 80% or more, specifically 85% or more, specifically 90% or more, more specifically 95% or more, even more specifically 97% or more, and even more specifically 99% or more hybridize with each other, while genes having a homology or identity lower than the above homology or identity do not hybridize with each other; or may include ordinary washing conditions of Southern hybridization, i.e., washing once, specifically two or three times, at a salt concentration and a temperature corresponding to 60° C., 1×SSC, and 0.1% SDS; specifically 60° C., 0.1×SSC, and 0.1% SDS; and more specifically 68° C., 0.1×SSC, and 0.1% SDS.

Although it is described herein as "a protein or polypeptide having or consisting of an amino acid sequence of a specific sequence number", it is apparent that a protein having an amino acid sequence with deletion, modification, substitution, conservative substitution, or addition in part of the sequence can be used in the present disclosure as long as the protein has an activity identical or corresponding to that of a polypeptide having or consisting of an amino acid sequence of the corresponding sequence number. For example, in the case of having the activity that is the same as or corresponding to that of the modified protein, it does not exclude an addition of a sequence upstream or downstream of the amino acid sequence, which does not alter the function of the protein, a mutation that may occur naturally, a silent mutation thereof, or a conservative constitution, and even when the sequence addition or mutation is present, it falls within the scope of the present disclosure.

As used herein, the "conservative substitution" means that an amino acid is substituted for another amino acid that has similar structural and/or chemical properties. Such amino acid substitutions may generally be made on the basis of similarity in polarity, charge, solubility, hydrophobicity, hydrophilicity and/or the amphipathic nature of the residues. For example, positively charged (basic) amino acids include arginine, lysine and histidine; negatively charged (acidic) amino acids include aspartic acid and glutamic acid; aromatic amino acids include phenylalanine, tryptophan and tyrosine; and hydrophobic amino acids include alanine, valine, isoleucine, leucine, methionine, phenylalanine, tyrosine and tryptophan.

Hybridization requires that two polynucleotides have complementary sequences, although mismatches between bases are possible depending on the stringency of the hybridization. The term "complementary" is used to describe the relationship between nucleotide bases that can hybridize with each other. For example, with respect to DNA, adenosine is complementary to thymine, and cytosine is complementary to guanine. Therefore, the present disclosure may also include an isolated polynucleotide fragment complementary to the entire sequence as well as a polynucleotide sequence substantially similar thereto.

Specifically, the polynucleotide having a homology or identity may be detected using hybridization conditions including a hybridization step at a $T_m$ value of 55° C. under the above-described conditions. Additionally, the $T_m$ value may be 60° C., 63° C., or 65° C., but is not limited thereto, and may be appropriately controlled by those skilled in the art depending on the purpose thereof.

The appropriate stringency for hybridizing polynucleotides depends on the length and degree of complementarity of the polynucleotides, and these variables are well known in the art (see Sambrook et al., supra, 9.50-9.51, 11.7-11.8).

As used herein, the term "homology" or "identity" refers to the degree of relevance between two given amino acid sequences or nucleotide sequences, and may be expressed as a percentage. The terms "homology" and "identity" are often used interchangeably with each other.

The sequence homology or identity of conserved polynucleotides or polypeptides may be determined by standard alignment algorithms and can be used together with a default gap penalty established by the program being used. Substantially, homologous or identical polynucleotides or polypeptides are generally expected to hybridize to all or at least about 50%, about 60%, about 70%, about 80% or about 90% of the entire length of the sequences under moderate or high stringent conditions. Polynucleotides that contain degenerate codons instead of codons in the hybridizing polynucleotides are also considered.

Whether any two polynucleotide or polypeptide sequences have a homology, similarity, or identity may be determined by a known computer algorithm such as the "FASTA" program (Pearson et al., (1988) [*Proc. Natl. Acad. Sci. USA* 85]: 2444) using default parameters. Alternatively, it may be determined by the Needleman-Wunsch algorithm (Needleman and Wunsch, 1970, *J. Mol. Biol.* 48: 443-453), which is performed using the Needleman program of the EMBOSS package (EMBOSS: The European Molecular Biology Open Software Suite, Rice et al., 2000, *Trends Genet.* 16: 276-277) (preferably, version 5.0.0 or versions thereafter) (GCG program package (Devereux, J., et al., *Nucleic Acids Research* 12: 387 (1984)), BLASTP, BLASTN, FASTA (Atschul, [S.] [F.,] [ET AL., *J MOLEC BIOL* 215]: 403 (1990); Guide to Huge Computers, Martin J. Bishop, [E D.,] *Academic Press*, San Diego, 1994, and [CARILLO ETA/.](1988) *SIAM J Applied Math* 48: 1073). Additionally, the homology, similarity, or identity may be determined using BLAST or ClustalW of the National Center for Biotechnology Information (NCBI).

The homology, similarity, or identity of polynucleotides or polypeptides may be determined by comparing sequence information using, for example, the GAP computer program, such as Needleman et al. (1970), *J Mol Biol.* 48: 443 as disclosed in Smith and Waterman, *Adv. Appl. Math* (1981) 2:482. In summary, the GAP program defines the homology, similarity, or identity as the value obtained by dividing the number of similarly aligned symbols (i.e. nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), *Nucl. Acids Res.* 14:6745, as disclosed in Schwartz and Dayhoff, eds., *Atlas of Protein Sequence and Structure*, National Biomedical Research Foundation, pp. 353-358, 1979; (2) a penalty of 3.0 for each gap and an additional 0.10 penalty for each symbol in each gap (or a gap opening penalty of 10 and a gap extension penalty of 0.5); and (3) no penalty for end gaps. Accordingly, as used herein, the term "homology" or "identity" refers to the relevance between sequences.

Another aspect of the present disclosure provides a polynucleotide encoding the tagatose-bisphosphate aldolase, and an expression vector including the polynucleotide, and a transformant including the expression vector.

As used herein, the term "polynucleotide" has a meaning which collectively includes DNA or RNA molecules. Nucleotides which are the basic structural units of polynucleotides include not only natural nucleotides but also modified analogs thereof in which sugar or base sites are modified (see, Scheit, Nucleotide Analogs, John Wiley, New York (1980); Uhlman and Peyman, Chemical Reviews, 90:543-584(1990)).

The polynucleotide may be a polynucleotide encoding a polypeptide having the amino acid sequence of SEQ ID NO: 1 of the present disclosure or a polynucleotide encoding a polypeptide having the fructose-4-epimerase activity while having a homology or identity of 85% or more to the SEQ ID NO: 1. Specifically, the polynucleotide encoding tagatose-bisphosphate aldolase consisting of the amino acid sequence of SEQ ID NO: 1 or an amino acid sequence having an identity of 85% or more thereto may be a polynucleotide having a homology or identity to the nucleotide sequence of SEQ ID NO:2 of at least 85%, 90%, 95%, 96%, 97%, 98%, 99% or 100%. Additionally, as described above, the polynucleotide of the present disclosure may include a polynucleotide which can be translated into the tagatose-bisphosphate aldolase of the present disclosure by codon degeneracy, and it is apparent that any polynucleotide which hybridizes with a polynucleotide consisting of a nucleotide sequence complementary to the nucleotide sequence of SEQ ID NO: 2 under stringent conditions to encode a polypeptide having the fructose-4-epimerase activity may be included without limitation.

The microorganism expressing the tagatose-bisphosphate aldolase, which can be used in the present disclosure, may be a microorganism including a recombinant vector containing the polynucleotide. The vector may be in a form operably linked to the polynucleotide of the present disclosure. As used above, the term "operably linked" refers to an operable linkage of a regulatory sequence for nucleotide expression with a nucleotide sequence encoding a target protein to perform general functions, which can affect the expression of the nucleotide sequence being encoded. Operable linkage with a vector may be prepared using a gene recombination technique known in the art, and site-specific DNA cleavage and ligation may be performed using a restriction enzyme, ligase, etc. known in the art.

As used herein, the term "vector" refers to any vehicle for cloning and/or transferring nucleotide sequence to an organism, for example, a host cell. A vector may be a replicon which allows for the replication of the fragments bound by binding with other DNA fragments. The term "replicon" as used herein refers to any genetic unit (for example, plasmid, phage, cosmid, virus), which can serve as a self-replicating unit for DNA replication in vivo, that is, capable of being replicated by self-regulation. The term "vector" may include a viral and non-viral vehicle for introducing a nucleotide sequence to an organism, for example, a host cell in vitro, ex vivo or in vivo, and may also include a mini-spherical DNA and a transposon such as Sleeping Beauty (Izsvak et al. *J. Mol. Biol.* 302:93-102 (2000)), or an artificial chromosome. Examples of conventionally used vectors may include natural or recombinant plasmids, cosmids, viruses, and bacteriophages. For example, as a phage vector or cosmid vector, pWE15, M13, MBL3, MBL4, IXII, ASHII, APII, t10, t11, Charon4A, Charon21A, etc., may be used, and as a plasmid vector, those based on pBR, pUC, pBluescriptII, pGEM, pTZ, pCL, pET, etc. may be used. The vector that can be used in the present disclosure is not particularly limited, and a known recombinant vector may be used. Additionally, the vector may be a recombinant which further includes various antibiotic resistance genes. As used herein, the term "antibiotic resistance gene" refers to a gene having resistance to antibiotics, and cells including this gene survive even in an environment treated with the corresponding antibiotic. Therefore, the antibiotic resistance gene is effectively used as a selection marker for a large-scale production of plasmids in *E. coli*. In the present disclosure, as the antibiotic resistance gene is not a factor that significantly affects the expression efficiency according to an optimal combination of vectors which is core technology of the present disclosure, and thus any commonly-used antibiotic resistance gene may be used as a selection marker without limitation. Specifically, a gene resistant to ampicillin, tetracycline, kanamycin, chloramphenicol, streptomycin, or neomycin may be used.

The microorganism expressing the tagatose-bisphosphate aldolase which can be used in the present disclosure may employ a method of introducing a vector including a polynucleotide encoding the enzyme into a host cell. The method of transforming the vector may include any method that can introduce a polynucleotide into a cell and may be performed by selecting a suitable standard technique known in the art. The method may include electroporation, calcium phosphate co-precipitation, retroviral infection, microinjection, DEAE-dextran, cationic liposome, heat shock, etc., but is not limited thereto.

As long as the transformed gene can be expressed in the host cell, it does not matter whether it is inserted into the chromosome of the host cell or located outside the chromosome, and both cases may be included. Additionally, the gene includes DNA and RNA as polynucleotides which can encode the polypeptide, and any gene can be used as long as it can be introduced into a host cell and expressed therein. For example, the gene may be introduced into a host cell in the form of an expression cassette, which is a polynucleotide construct including all elements necessary for self-expression. The expression cassette may conventionally include a promoter operably linked to the gene, a transcription termination signal, a ribosome-binding domain, and a translation termination signal. The expression cassette may be in the form of a recombinant vector capable of self-replication. Additionally, the gene may be introduced into a host cell as is or in the form of a polynucleotide construct and operably linked to a sequence necessary for its expression in the host cell.

The microorganism of the present disclosure may include any prokaryotic and eukaryotic microorganisms as long as it is a microorganism capable of producing the tagatose-bisphosphate aldolase of the present disclosure including the polynucleotide or the recombinant vector of the present disclosure. For example, the microorganism may include a microorganism strain belonging to *Escherichia* sp., *Erwinia* sp., *Serratia* sp., *Providencia* sp., *Corynebacterium* sp., and *Brevibacterium* sp., and specifically, the microorganism may be *E. coli*, or *Corynebacterium glutamicum*, but is not limited thereto.

The microorganism of the present disclosure may include all microorganisms which can express the tagatose-bisphosphate aldolase of the present disclosure by various known methods in addition to the introduction of the polynucleotide or the vector.

The culture of the microorganism of the present disclosure may be prepared by culturing the microorganism expressing the tagatose-bisphosphate aldolase of the present disclosure in a medium.

As used herein, the term "cultivation" refers to growing the microorganism in an appropriately adjusted environment. The cultivation process of the present disclosure may be achieved according to an appropriate medium and culture condition known in the art. The cultivation process may be used by easily adjusting cultivation conditions according to the microbial strain being selected by one of ordinary skill in the art. The cultivation of the microorganism may be performed in a batch process, continuous process, fed-batch process, etc. known in the art, but the cultivation process is not particularly limited thereto. In particular, with respect to the cultivation conditions, the pH of the culture may be adjusted to a suitable pH (e.g., pH 5 to 9, specifically pH 7 to 9) using a basic compound (e.g., sodium hydroxide, potassium hydroxide, or ammonia) or acidic compound (e.g., phosphoric acid or sulfuric acid). Additionally, an antifoaming agent, such as fatty acid polyglycol ester, may be used to prevent foam generation during cultivation. Additionally, the aerobic condition of the culture may be maintained by introducing oxygen or an oxygen-containing gas mixture to the culture, or the anaerobic and microaerobic states of the culture may be maintained by introducing nitrogen, hydrogen, or carbon dioxide gas to the culture without the injection of a gas. The cultivation temperature may be maintained at 20 to 45° C., specifically at 30 to 37° C., but the cultivation temperature is not limited thereto. The cultivation may be continued until the production of a useful material is obtained, and specifically for 10 hours to 160 hours, but the cultivation conditions are not limited thereto and specifically for about 0.5 hours to 60 hours, but the cultivation time is not limited to the above. Additionally, as the carbon sources to be used in the culture medium, sugars and carbohydrates (e.g., glucose, sucrose, lactose, fructose, maltose, molasses, starch, and cellulose); oils and fats (e.g., soybean oil, sunflower oil, peanut oil, and coconut oil); fatty acids (e.g., palmitic acid, stearic acid, and linoleic acid); alcohols (e.g., glycerol and ethanol); and organic acids (e.g., acetic acid), etc. may be used alone or in combination, but are not limited thereto. As the nitrogen sources to be used in the culture medium, nitrogen-containing organic compounds (e.g., peptone, yeast extract, meat juice, malt extract, corn steep liquor, soybean flour, and urea) or inorganic compounds (e.g., ammonium sulfate, ammonium chloride, ammonium phosphate, ammonium carbonate, and ammonium nitrate), etc. may be used alone or in combination, but are not limited thereto. As the phosphorus sources to be used in the culture medium, potassium dihydrogen phosphate, dipotassium hydrogen phosphate, corresponding sodium-containing salts, etc. may be used alone or in combination, but are not limited thereto. Additionally, metal salts (e.g., magnesium sulfate or iron sulfate), amino acids, vitamins, etc., which are essential growth-promoting materials, may be contained in the culture medium.

The composition for producing tagatose of the present disclosure includes tagatose-bisphosphate aldolase having fructose-4-epimerization activity, which directly converts fructose into tagatose, a microorganism expressing the tagatose-bisphosphate aldolase, or a culture of the microorganism, and may be characterized in that enzymes other than fructose as a substrate are not contained.

The composition for producing tagatose of the present disclosure may further include any suitable excipient commonly used in the composition for producing tagatose. The excipient may include, for example, a preservative, a wetting agent, a dispersing agent, a suspending agent, a buffer, a stabilizing agent, an isotonic agent, etc., but is not limited thereto.

The composition for producing tagatose of the present disclosure may further include a metal. In one embodiment, the metal of the present disclosure may be a metal containing a divalent cation. Specifically, the metal of the present disclosure may be nickel (Ni), magnesium (Mg), or manganese (Mn). More specifically, the metal of the present disclosure may be a metal ion or a metal salt, and even more specifically, the metal may be selected from the group consisting of manganese and nickel, and much more specifically, the metal salt may be $MgSO_4$, $NiSO_4$, $NiCl_2$, $MgCl_2$, $MnCl_2$, or $MnSO_4$.

Still another aspect of the present disclosure provides a method of producing tagatose, including converting fructose into tagatose by contacting fructose with at least one of tagatose-bisphosphate aldolase derived from *Caldilinea* sp.; a microorganism expressing the tagatose-bisphosphate aldolase; or a culture of the microorganism. The terms "tagatose-bisphosphate aldolase" and "microorganism" are as described above.

In one embodiment, the contact of the present disclosure may be performed under a pH condition of pH 5.0 to 9.0 and a temperature condition of 30° C. to 80° C. and/or for 0.5 hours to 48 hours.

Specifically, the contact of the present disclosure may be performed under a pH condition of pH 6.0 to 9.0 or pH 7.0 to 9.0. Additionally, the contact of the present disclosure may be performed at a temperature condition of 35 to 80° C., 40 to 80° C., 45 to 80° C., 50 to 80° C., 55 to 80° C., 60 to 80° C., 30 to 70° C., 35 to 70° C., 40 to 70° C., 45 to 70° C., 50 to 70° C., 55 to 70° C., 60 to 70° C., 30 to 65° C., 35 to 65° C., 40 to 65° C., 45 to 65° C., 50 to 65° C., 55 to 65° C., 30 to 60° C., 35 to 60° C., 40 to 60° C., 45 to 60° C., 50 to 60° C. or 55 to 60° C. Further, the contact of the present disclosure may be performed for duration of 0.5 hours to 36 hours, 0.5 hours to 24 hours, 0.5 hours to 12 hours, 0.5 hours to 6 hours, 1 hour to 48 hours, 1 hour to 36 hours, 1 hour to 24 hours, 1 hour to 12 hours, 1 hour to 6 hours, 3 hours to 48 hours, 3 hours to 36 hours, 3 hours to 24 hours, 3 hours to 12 hours, 3 hours to 6 hours, 6 hours to 48 hours, 6 hours to 36 hours, 6 hours to 24 hours, 6 hours to 12 hours, 12 hours to 48 hours, 12 hours to 36 hours, 12 hours to 24 hours, 18 hours to 48 hours, 18 hours to 36 hours, or 18 hours to 30 hours.

In one embodiment, the contact of the present disclosure may be performed in the presence of a metal. The applicable metal is the same as those in the above-described embodiment.

In another embodiment, the method for producing tagatose of the present disclosure may include converting fructose into tagatose by further contacting fructose with a metal ion or a metal salt. Specifically, the metal may be at least one selected from the group consisting of manganese and nickel.

The production method of the present disclosure may further include separation and/or purification of tagatose. The separation and/or purification may be performed by a method commonly used in the art, and non-limiting examples thereof include dialysis, precipitation, adsorption, electrophoresis, ion exchange chromatography, and fractional crystallization, etc. The purification method may be performed only by a single method or by two or more methods in combination.

Additionally, the production method of the present disclosure may further include decolorization and/or desalination, before or after the separation and/or purification. By performing the decolorization and/or desalination, it is possible to obtain tagatose with higher quality.

In still another embodiment, the production method of the present disclosure may further include crystallization of tagatose, after conversion of fructose into tagatose, separation and/or purification, or decolorization and/or desalination of the present disclosure. The crystallization may be performed by a commonly-used crystallization method. For example, the crystallization may be performed by cooling crystallization.

In still another embodiment, the production method of the present disclosure may further include concentrating tagatose, before the crystallization. The concentration may increase the crystallization efficiency.

In still another embodiment, the production method of the present disclosure may further include contacting unreacted fructose with the enzyme of the present disclosure, the microorganism expressing the enzyme, or the culture of the microorganism after the separation and/or purification, and reusing a mother solution, from which crystals have been separated, in the separation and/or purification after the crystallization of the present disclosure, or a combination thereof.

Mode for Carrying Out the Invention

The present disclosure will be described in more detail by way of Examples and Experimental Examples. However, these Examples and Experimental Examples are given for illustrative purposes only, and the scope of the invention is not intended to be limited to or by these Examples and Experimental Examples.

EXAMPLE 1

Preparation of Recombinant Expression Vector and Transformant including Gene Encoding Novel Tagatose-Bisphosphate Aldolase In order to provide a novel heat-resistant fructose-4-epimerase, typically, information of tagatose-bisphosphate aldolase genes derived from *Caldilinea aerophila* DSM 14535 belonging to *Caldilinea* sp. was obtained to prepare vectors which can be expressed in *E. coli* and transformed microorganisms.

Specifically, a gene sequence of tagatose-bisphosphate aldolase was selected from gene sequences of *Caldilinea aerophila* DSM 14535, which are registered in Kyoto Encyclopedia of Genes and Genomes (KEGG) and National Center for biotechnology Information (NCBI), and based on the amino acid sequence (SEQ ID NO: 1) and the nucleotide sequence (SEQ ID NO: 2) of the microorganism, and a recombinant expression vector pBT7-C-His-CJ_CA_F4E which can be expressed in *E. coli* including the nucleotide sequence of the enzyme was prepared (Bioneer Corp. Korea).

The thus-prepared recombinant vector was transformed into *E. coli* BL21(DE3) by heat shock transformation (Sambrook and Russell: Molecular cloning, 2001), and kept frozen in 50% glycerol before use. The transformed strain was designated as *E. coli* BL21(DE3)/CJ_CA_F4E and deposited at the Korean Culture Center of Microorganisms (KCCM), which is an international depositary authority under the provisions of the Budapest Treaty, on Aug. 11, 2017 with Accession No. KCCM12094P.

EXAMPLE 2

Preparation and Purification of Recombinant Enzyme

In order to prepare a recombinant enzyme from *E. coli* BL21(DE3)/CJ_CA_F4E, which is the transformed strain prepared in Example 1, the transformed microorganism was seeded in a culture tube containing 5 mL of an LB liquid medium supplemented with ampicillin antibiotic, and then seed culture was performed in a shaking incubator at 37° C. until absorbance at 600 nm reached 2.0. The culture solution obtained by the seed culture was seeded in a culture flask containing a liquid medium containing LB and lactose, which is a protein expression regulator, and then main culture was performed. The seed culture and the main culture were performed under conditions of 180 rpm and 37° C. Then, the culture solution was centrifuged at 8,000 rpm and at 4° C. for 20 minutes to recover cells. The recovered cells were washed with 50 mM Tris-HCl (pH 8.0) buffer twice and re-suspended in 50 mM $NaH_2PO_4$ (pH 8.0) buffer containing 10 mM imidazole and 300 mM NaCl. The re-suspended cells were disrupted using a sonicator and cell lysates were centrifuged at 13,000 rpm and 4 C for 20 minutes to obtain only supernatant. The supernatant was purified by His-tag affinity chromatography, and 10 column volumes of 50 mM $NaH_2PO_4$ (pH 8.0) buffer containing 20 mM imidazole and 300 mM NaCl was applied to remove non-specifically bound proteins. Subsequently, 50 mM $NaH_2PO_4$ (pH 8.0) buffer containing 250 mM imidazole and 300 mM NaCl was further applied to perform elution. Then, dialysis was performed using 50 mM Tris-HCl (pH8.0) buffer to obtain CJ RP F4E, a purified enzyme for enzyme characterization.

EXAMPLE 3

Conversion from Fructose into Tagatose and Evaluation of Activity thereof.

In order to measure the fructose-4-epimerization activity of CJ_CA_F4E, which is the recombinant enzyme of the present disclosure obtained in Example 2, 50 mM Tris-HCl (pH 8.0), 1 mM $NiSO_4$, and 20 mg/mL of CJ_CA_F4E were added to 30% by weight of fructose, and the mixture was allowed to react at 60° C. for 10 hours.

Then, the residual fructose after the reaction and tagatose, the reaction product, were quantified by HPLC. The HPLC analysis was performed as follows: Shodex Sugar SP0810 was used as a column, a temperature of the column was 80° C., and water as a mobile phase was applied at a flow rate of 1 mL/min (FIG. 1).

As a result, it was confirmed that the conversion rate from fructose into tagatose by the enzymatic reaction of CJ_CA_F4E of the present disclosure was 1.6%.

EXAMPLE 4

Evaluation of Activity of Recombinant Enzyme According to Temperature

In order to examine the effect of temperature on the fructose-4-epimerization activity of CJ_CA_F4E prepared in Example 2, 1 mg/mL of CJ_CA_F4E was added to 50 mM Tris HCl (pH 8.0) buffer containing 10% by weight of fructose, and allowed to react at different temperatures of 45° C., 50° C., 55° C., 60° C., 65° C. and 70° C. for 3 hours. After the reaction was completed, tagatose in the reacted solution was quantified by HPLC.

Figure 2:
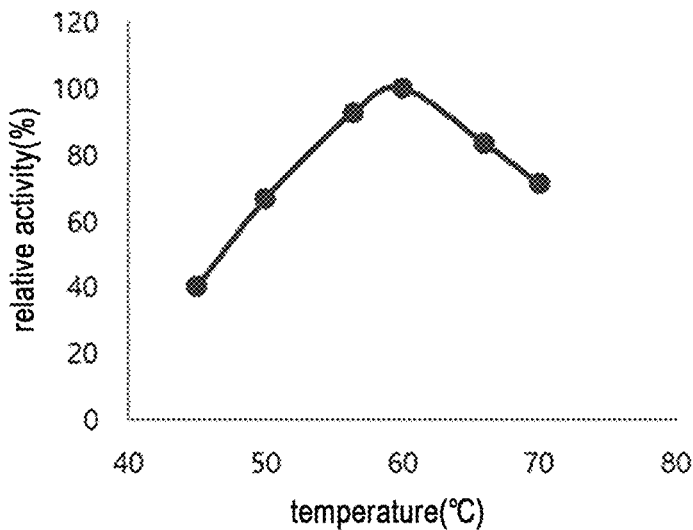
FIG. 2 is a graph showing fructose-4-epimerization activity of tagatose-bisphosphate aldolase (CJ_CA_F4E) of the present disclosure according to temperature changes.

As a result, CJ_CA_F4E showed its maximum activity at 60° C., and maintained 80% or more of its maximum activity at 55° C. to 65° C. and 40% or more of its maximum activity in all temperature ranges (FIG. 2).

EXAMPLE 5

Evaluation of Activity of Recombinant Enzyme of the Present Disclosure According to Addition of Metals In order to examine the effect of metal ions on the fructose-4-epimerization activity of CJ_CA_F4E prepared in Example 2, 1 mg/mL of CJ_CA_F4E and 1 mM of various metal ions ($ZnSO_4$, $MgCl_2$, $MnCl_2$, $NH_4Cl$, $CaCl_2$, $Na_2SO_4$, $CuSO_4$, $MgSO_4$, $MnSO_4$, $(NH_4)_2SO_4$ or $NiSO_4$)) were added to 50 mM Tris HCl (pH 8.0) buffer containing 10% by weight of fructose, and allowed to react at 60° C. for 5 hours. After the reaction was completed, tagatose in the reacted solution was quantified by HPLC.

Figure 3:
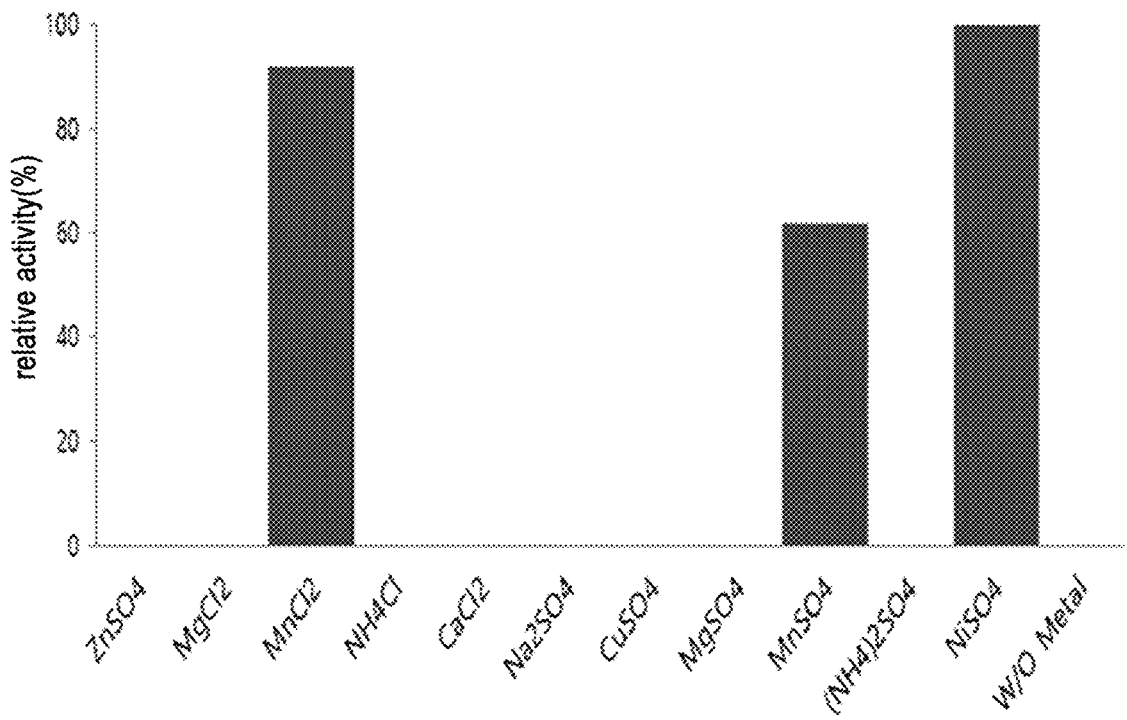
FIG. 3 is a graph showing fructose-4-epimerization activity of tagatose-bisphosphate aldolase (CJ_CA_F4E) of the present disclosure according to addition of metals.

As a result, the activity of CJ_CA_F4E was increased by addition of each of $MnCl_2$, $MnSO_4$ and $NiSO_4$, indicating that the manganese or nickel ion can increase the activity of CJ_CA_F4E (FIG. 3).

Those of ordinary skill in the art will recognize that the present disclosure may be embodied in other specific forms without departing from its spirit or essential characteristics. The described embodiments are to be considered in all respects only as illustrative and not restrictive. The scope of the present disclosure is therefore indicated by the appended claims rather than by the foregoing description. All changes which come within the meaning and range of equivalency of the claims are to be embraced within the scope of the present disclosure.

The invention claimed is:

1. A method for producing tagatose, the method consisting of contacting fructose with an isolated *Caldilinea* sp. tagatose-bisphosphate aldolase to convert the fructose into tagatose, wherein the isolated *Caldilinea* sp. tagatose-bisphosphate aldolase has fructose-4-epimerase activity.

2. The method of claim 1, wherein the contacting is performed at a pH of 7.0 to 9.0 and at a temperature of 45° C. to 80° C. for 0.5 hours to 24 hours.

3. The method of claim 1, wherein the *Caldilinea* sp. tagatose-bisphosphate aldolase comprises the amino acid sequence of SEQ ID NO: 1 or an amino acid sequence having 80% or more sequence identity to the amino acid sequence of SEQ ID NO: 1.

* * * * *

SEQUENCE LISTING

```
<160> NUMBER OF SEQ ID NOS: 2

<210> SEQ ID NO 1
<211> LENGTH: 408
<212> TYPE: PRT
<213> ORGANISM: Artificial Sequence
<220> FEATURE:
```

<223> OTHER INFORMATION: Amino acid sequence of CA-F4E

<400> SEQUENCE: 1

```
Met Ser Thr Leu Arg His Ile Ile Leu Arg Leu Ile Glu Leu Arg Glu
1               5                   10                  15

Arg Glu Gln Ile His Leu Thr Leu Leu Ala Val Cys Pro Asn Ser Ala
            20                  25                  30

Ala Val Leu Glu Ala Ala Val Lys Val Ala Ala Arg Cys His Thr Pro
        35                  40                  45

Met Leu Phe Ala Ala Thr Leu Asn Gln Val Asp Arg Asp Gly Gly Tyr
    50                  55                  60

Thr Gly Trp Thr Pro Ala Gln Phe Val Ala Glu Met Arg Arg Tyr Ala
65                  70                  75                  80

Val Arg Tyr Gly Cys Thr Thr Pro Leu Tyr Pro Cys Leu Asp His Gly
                85                  90                  95

Gly Pro Trp Leu Lys Asp Arg His Ala Gln Glu Lys Leu Pro Leu Asp
            100                 105                 110

Gln Ala Met His Glu Val Lys Leu Ser Leu Thr Ala Cys Leu Glu Ala
        115                 120                 125

Gly Tyr Ala Leu Leu His Ile Asp Pro Thr Val Asp Arg Thr Leu Pro
    130                 135                 140

Pro Gly Glu Ala Pro Leu Val Pro Ile Val Val Glu Arg Thr Val Glu
145                 150                 155                 160

Leu Ile Glu His Ala Glu Gln Glu Arg Gln Arg Leu Asn Leu Pro Ala
                165                 170                 175

Val Ala Tyr Glu Val Gly Thr Glu Val His Gly Gly Leu Val Asn
            180                 185                 190

Phe Asp Asn Phe Val Ala Phe Leu Asp Leu Leu Lys Ala Arg Leu Glu
        195                 200                 205

Gln Arg Ala Leu Met His Ala Trp Pro Ala Phe Val Val Ala Gln Val
    210                 215                 220

Gly Thr Asp Leu His Thr Thr Tyr Phe Asp Pro Ser Ala Ala Gln Arg
225                 230                 235                 240

Leu Thr Glu Ile Val Arg Pro Thr Gly Ala Leu Leu Lys Gly His Tyr
                245                 250                 255

Thr Asp Trp Val Glu Asn Pro Ala Asp Tyr Pro Arg Val Gly Met Gly
            260                 265                 270

Gly Ala Asn Val Gly Pro Glu Phe Thr Ala Ala Glu Phe Glu Ala Leu
        275                 280                 285

Glu Ala Leu Glu Arg Arg Glu Gln Arg Leu Cys Ala Asn Arg Lys Leu
    290                 295                 300

Gln Pro Ala Cys Phe Leu Ala Ala Leu Glu Glu Ala Val Val Ala Ser
305                 310                 315                 320

Asp Arg Trp Arg Lys Trp Leu Gln Pro Asp Glu Ile Gly Lys Pro Phe
                325                 330                 335

Ala Glu Leu Thr Pro Ala Arg Arg Trp Leu Val Gln Thr Gly Ala
            340                 345                 350

Arg Tyr Val Trp Thr Ala Pro Lys Val Ile Ala Ala Arg Glu Gln Leu
        355                 360                 365

Tyr Ala His Leu Ser Leu Val Gln Ala Asp Pro His Ala Tyr Val Val
    370                 375                 380

Glu Ser Val Ala Arg Ser Ile Glu Arg Tyr Ile Asp Ala Phe Asn Leu
385                 390                 395                 400
```

Tyr Asp Ala Ala Thr Leu Leu Gly
            405

<210> SEQ ID NO 2
<211> LENGTH: 1227
<212> TYPE: DNA
<213> ORGANISM: Artificial Sequence
<220> FEATURE:
<223> OTHER INFORMATION: Nucleic acid sequence of CA-F4E

<400> SEQUENCE: 2

```
atgtcaacac ttcgccacat cattttgcga ctgatcgagc tgcgtgaacg agaacagatc      60
catctcacgc tgctggccgt ctgtcccaac tcggcggcgg tgctggaggc agcggtgaag     120
gtcgccgcgc gctgccacac gccgatgctc ttcgctgcca cgctcaatca agtcgatcgc     180
gacggcggct acaccggttg gacgcctgcg caattcgtcg ccgagatgcg tcgctatgcc     240
gtccgctatg gctgcaccac cccgctctat ccttgcctgg atcacggcgg gccgtggctc     300
aaagatcgcc atgcacagga aaagctaccg ctcgaccagg cgatgcatga ggtcaagctg     360
agcctcaccg cctgtctgga ggccggctac gcgctgctgc acatcgaccc cacggtcgat     420
cgcacgctcc cgcccggaga agcgccgctc gtgccgatcg tcgtcgagcg cacggtcgag     480
ctgatcgaac atgccgaaca ggagcgacag cggctgaacc tgccggcggt cgcctatgaa     540
gtcggcaccg aagaagtaca tggcgggctg gtgaatttcg acaattttgt cgccttcttg     600
gatttgctca aggcaaggct tgaacaacgt gccctgatgc acgcctggcc cgccttcgtg     660
gtggcgcagg tcggcactga cctgcataca acgtattttg accccagtgc ggcgcaacgg     720
ctgactgaga tcgtgcgccc taccggtgca ctgttgaagg ggcactacac cgactgggtc     780
gaaaatcccg ccgactatcc gagggtaggc atgggaggcg ccaacgttgg tccagagttt     840
acggcggccg agttcgaggc gctggaagcg ctggaacggc gggaacaacg gctgtgcgcc     900
aaccggaaat tgcagcccgc ctgtttttttg gctgcactgg aagaggcagt agtcgcttca     960
gatcgttggc ggaagtggct ccagcccgat gagatcggca agcccttttgc agaattaacg    1020
cccgcacgcc ggcgctggct cgtgcagacc ggggcacgct acgtctggac tgcgccgaaa    1080
gttatcgccg cacgcgaaca gctctatgcg cacctctccc ttgtgcaggc ggatccacat    1140
gcctacgtgg tagagtcagt cgcccggtca atcgagcgct atatcgatgc cttcaactta    1200
tacgacgccg ctacattgct tggatga                                        1227
```